| United States Patent [19] | [11] | 4,334,107 |
|---|---|---|
| Van Peppen | [45] | Jun. 8, 1982 |

[54] CATALYTIC PURIFICATION OF PHENOL

[75] Inventor: Jan F. Van Peppen, Chester, Va.

[73] Assignee: Allied Chemical Corporation, Morris Township, Morris County, N.J.

[21] Appl. No.: 208,903

[22] Filed: Nov. 21, 1980

[51] Int. Cl.³ .................. C07C 37/86; C07C 45/00
[52] U.S. Cl. .................................. 568/749; 568/486
[58] Field of Search .............. 568/749, 754, 768, 798, 568/742, 803, 486

[56] References Cited

U.S. PATENT DOCUMENTS

| 2,992,169 | 7/1961 | Gregory et al. | |
|---|---|---|---|
| 3,076,810 | 2/1963 | Duggan et al. | |
| 3,120,149 | 8/1964 | Barry | 568/754 |
| 3,290,384 | 12/1966 | Largman et al. | |
| 3,305,586 | 2/1967 | Phielix | |
| 3,437,699 | 4/1969 | Flickinger | 568/754 |
| 3,441,618 | 4/1969 | Flickinger | 568/754 |
| 3,454,653 | 7/1969 | Karson | 568/754 |
| 3,692,845 | 9/1972 | Cheema et al. | |
| 3,965,187 | 2/1976 | Little et al. | |

FOREIGN PATENT DOCUMENTS

| 621040 | 5/1961 | Canada | 568/754 |
|---|---|---|---|
| 1121621 | 1/1962 | Fed. Rep. of Germany | 568/754 |
| 2644318 | 4/1978 | Fed. Rep. of Germany | 568/754 |
| 865677 | 4/1961 | United Kingdom | 568/754 |

Primary Examiner—Werren B. Lone
Attorney, Agent, or Firm—Richard A. Anderson

[57] ABSTRACT

A method is disclosed to purify crude phenol containing acetol and alpha-methyl styrene prior to hydrogenation to cyclohexanone comprising
  contacting the crude phenol with a catalyst while heating the crude phenol and catalyst to a temperature between about 140° C. and 190° C.
  at a pressure between about atmospheric and about 70 psig
  in an inert atmosphere
so that the catalyst causes a reaction between the impurities acetol and alpha-methyl styrene to form cumene and pyruvic aldehyde, then
  heating the resultant compounds for a period of 0.1 to about 6 hours under an inert gas sweep at a temperature of from about 150° C. to about 190° C. until the pyruvic aldehyde has decomposed and its decomposition products are swept away in the gas sweep.

6 Claims, No Drawings

CATALYTIC PURIFICATION OF PHENOL

BACKGROUND OF THE INVENTION

This invention relates to the purification of phenol produced by the oxidation of cumene, more specifically, the removal of acetol and alphamethyl styrene from crude phenol by reaction in the presence of a catalyst, to purify for the subsequent hydrogenation of phenol process.

Production of phenol by oxidation of cumene is known, such as in U.S. Pat. No. 3,290,384 hereby incorporated by reference. The subsequent hydrogenation of phenol to cyclohexanone is known, such as in U.S. Pat. No. 3,076,810, or for the vapor phase process, U.S. Pat. No. 3,305,586, both hereby incorporated by reference. Various processes for purification of phenol prior to hydrogenation are also known, such as in U.S. Pat. No. 3,965,187; U.S. Pat. No. 2,992,169 and U.S. Pat. No. 3,692,845, all hereby incorporated by reference.

Phenol produced by the cumene oxidation process contains constituents which lower the rate of hydrogenation relative to a purified phenol. Additionally, these constituents generate carbon monoxide. Carbon monoxide is known to deactivate the catalyst used in the phenol hydrogenation process (palladium on carbon or other support). When the phenol produced from cumene was pretreated with diand polyfunctional aliphatic, alicyclic or aromatic amines and then distilled, the harmful constituents were apparently removed as the rate of hydrogenation was relatively high and only very small amounts of carbon monoxide were generated during the hydrogenation reaction.

SUMMARY OF THE INVENTION

We have now found that when the phenol produced from cumene was heated to 180° C. in the presence of palladium on carbon catalyst, while nitrogen was purged through the reaction mixture, carbon monoxide was generated. When the carbon monoxide generated had subsided and the nitrogen purge was replaced by hydrogen, the rate of hydrogenation at 160° C. was as fast as that of phenol pretreated with the di- and polyfunctional amines followed by distillation. Also when acetol was added to phenol pretreated with di- and polyfunctional amines the generation of carbon monoxide was very high.

It has been observed that acetol and alpha-methyl styrene, both constituents in phenol produced from cumene, can react to form cumene and pyruvic aldehyde. The latter may decompose into carbon monoxide and acetaldehyde as shown in the following reaction equation:

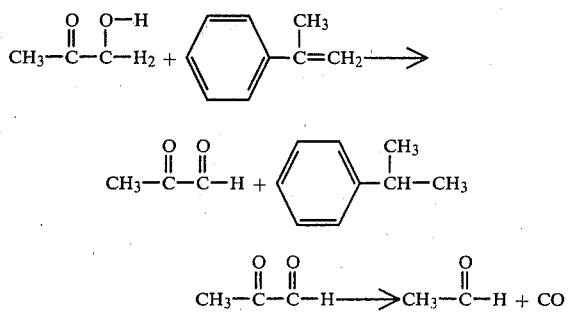

The reaction of acetol with alpha-methyl styrene to form cumene does not proceed without catalyst. Palladium on carbon was found to be effective; nickel (supported and Raney-type) was not. The reaction involves the transfer of one mole of hydrogen from acetol to alpha-methyl styrene. The dehydrogenation product from acetol, presumably pyruvic aldehyde

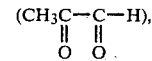

was not stable under reaction conditions. Other noble metal catalysts or palladium on other supports capable of catalyzing the hydrogen transfer reaction between acetol and alphamethyl styrene may also be used in the invention. Other supports are aluminum oxide or silica, and other noble metals are platinum, rhodium or ruthenium. The reaction can be carried out at 160° C. The acetol and alpha-methyl styrene are byproducts in the cumene oxidation process to phenol. They are believed to be formed as shown in the following scheme:

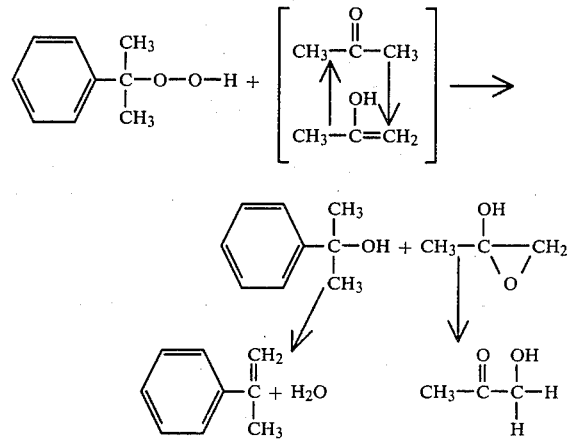

On the assumption that acetol and alpha-methyl styrene are formed by the above scheme only, the molar ratio of these two should, therefore, be 1:1. Both compounds are nuisance byproducts. Acetol poisons the catalyst in the phenol hydrogenation and alpha-methyl styrene is difficult to remove in the phenol rectification and from the cumene recycled in the process. Taking advantage of the discovered reaction of this invention, the removal of these byproducts can be facilitated.

Specifically, the invention is a method to purify crude phenol containing acetol and alpha-methyl styrene prior to hydrogenation comprising contacting the crude phenol with catalyst while
heating the crude phenol and catalyst to a temperature between about 140° C. and about 190° C., more specifically between 160° C. and 183° C.
at a pressure between about atmospheric and about 70 psig
in an inert atmosphere
so that the catalyst causes a reaction between the impurities acetol and alpha-methyl styrene to form cumene and pyruvic aldehyde, then
heating the resultant compounds at a pressure between atmospheric and about 70 psig for a period of 0.1 to about six hours, more preferably for a period of 2 to 4 hours, under an inert gas sweep to a temperature of from about 150° C. to about 190° C., more preferably between 160° C. and 183° C., until the pyruvic aldehyde has decomposed and its decomposition products are swept away in the gas sweep.

The catalyst effective in the reaction between acetol and alpha-methyl styrene is palladium on carbon or any other catalyst capable of catalyzing the hydrogen transfer between acetol and alpha-methyl styrene.

In a commercial continuous process, heated crude phenol would be continuously passed across heated catalyst to continuously convert the impurities to pyruvic aldehyde and cumene, while the previously formed pyruvic aldehyde would continuously decompose and be continuously removed with an inert nitrogen sweep.

DESCRIPTION OF THE PREFERRED EMBODIMENT

Charged to an autoclave were 9,000 parts of phenol, 500 parts of alpha-methyl styrene, 500 parts of acetol and 32 parts of 5 percent palladium on carbon catalyst. The mixture was heated to 160° C. under 54 psig nitrogen pressure while agitated. Samples were withdrawn after 0.5 hour, 2 hours and 4 hours. Analysis by gas phase chromatography showed the disappearance of alpha-methyl styrene and acetol and the formation of cumene. These results were confirmed by mass spectrometry. The conversions appeared to be complete after four hours.

I claim:

1. A method to purify crude phenol containing acetol and alpha-methyl styrene prior to hydrogenation comprising
    contacting the crude phenol with a catalyst while heating the crude phenol and catalyst to a temperature between about 140° C. and about 190° C.
    at a pressure between about atmospheric and about 70 psig.
    in an inert atmosphere
    so that the catalyst causes a reaction between the impurities acetol and alpha-methyl styrene to form cumene and pyruvic aldehyde, then
    heating the resultant compounds for a period of 0.1 to about six hours under an inert gas sweep to a temperature of from about 150° C. to about 190° C. until the pyruvic aldehyde decomposes and its decomposition products are swept away in the gas sweep,
    and said catalyst is selected from the group consisting of palladium, platinum, rhodium and ruthenium supported on a support selected from the group consisting of carbon, aluminum oxide and silica.

2. The method of claim 1 wherein the catalyst is palladium on a carbon support.

3. The method of claim 1 wherein the crude phenol and the catalyst are heated to a temperature between about 160° C. and 183° C. and likewise the resultant compounds are heated to a temperature between about 160° C. and 183° C. at a pressure between about atmospheric and about 70 psig.

4. The method of claim 1 wherein the heating of the crude phenol and the catalyst is carried out for a period of from about 2 to about 4 hours, and likewise the resultant compounds are heated for a period of from about 2 to about 4 hours.

5. The method of claim 2 wherein the process is continuous and both heating steps are carried out at a temperature of from about 160° C. to 183° C. for a period of about 2 to about 4 hours.

6. The continuous process of claim 5 wherein both heating steps are carried out simultaneously.

* * * * *